US006030162A

United States Patent [19]

Huebner

[11] Patent Number: 6,030,162

[45] Date of Patent: Feb. 29, 2000

[54] AXIAL TENSION SCREW

[75] Inventor: Randall J. Huebner, Aloha, Oreg.

[73] Assignee: Acumed, Inc., Beaverton, Oreg.

[21] Appl. No.: 09/216,316

[22] Filed: Dec. 18, 1998

[51] Int. Cl.[7] .............................. F16B 35/04; F16B 39/28

[52] U.S. Cl. .......................... 411/413; 411/263; 411/395; 411/426; 606/73

[58] Field of Search .................................... 411/263, 307, 411/308, 309, 310, 395, 412, 413, 426; 606/73

[56] References Cited

U.S. PATENT DOCUMENTS

| | | |
|---|---|---|
| 65,651 | 6/1867 | Davies . |
| 146,023 | 12/1873 | Russell . |
| 197,467 | 11/1877 | Harvey . |
| 197,933 | 12/1877 | Harvey . |
| D. 356,868 | 3/1995 | Broberg et al. . |
| 1,980,093 | 11/1934 | Rosenberg . |
| 2,146,023 | 2/1939 | Lounsbury . |
| 2,165,149 | 7/1939 | Olson . |
| 2,356,098 | 8/1944 | Steinle et al. . |
| 2,377,405 | 6/1945 | Davies . |
| 2,382,019 | 8/1945 | Miller . |
| 2,383,231 | 8/1945 | Anderton . |
| 2,419,555 | 4/1947 | Fator . |
| 2,633,091 | 3/1953 | Wenger et al. . |
| 2,801,631 | 8/1957 | Charnley . |
| 2,842,180 | 7/1958 | Brown et al. . |
| 3,051,169 | 8/1962 | Grath . |
| 3,079,181 | 2/1963 | van der Wissel . |
| 3,124,408 | 3/1964 | Oestereicher . |
| 3,233,500 | 2/1966 | de Vellier . |
| 3,454,070 | 7/1969 | Phipard, Jr. . |

(List continued on next page.)

FOREIGN PATENT DOCUMENTS

| | | |
|---|---|---|
| 731381 | 4/1966 | Canada . |
| 1007493 | 3/1977 | Canada . |
| 0172130A2 | 2/1986 | European Pat. Off. . |
| 2588332A | 4/1987 | France . |
| 2618344 | 11/1976 | Germany . |
| 3215228A1 | 11/1983 | Germany . |
| 3630863A1 | 3/1988 | Germany . |
| 4021550A1 | 1/1991 | Germany . |
| 365613 | 12/1938 | Italy . |
| 598490 | 10/1959 | Italy . |
| 45-24729 | 8/1970 | Japan . |
| 77837 | 6/1918 | Switzerland . |
| 1034734 | 8/1983 | U.S.S.R. . |
| 1216466A | 3/1986 | U.S.S.R. . |
| 1718877A1 | 3/1992 | U.S.S.R. . |
| 598834 | 2/1948 | United Kingdom . |
| 1389427 | 11/1972 | United Kingdom . |
| WO89/09030 | 10/1989 | WIPO . |
| WO90/02526 | 3/1990 | WIPO . |
| WO93/00518 | 1/1993 | WIPO . |

OTHER PUBLICATIONS

The Herbert™ Bone Screws for Small Bone Fractures, Fracture Management, 97–1152–01 12.5MI printed in U.S.A. © 1992 Zimmer, Inc.

Toby et al., "A Comparison of Fixation Screws for the Scaphoid During Application of Cyclical Bending Loads," *The Journal of Bone and Joint Surgery,* vol. 79–A, No. 8, pp. 1190–1197, Aug. 1997.

Haddad et al., "Acute Percutaneous Scaphoid Fixation," *The Journal of Bone and Joint Surgery,* vol. 80–B, No. 1, pp. 95–99, Jan. 1998.

Wheeler et al., "Biomechanical Assessment of Compression Screws," *Clinical Orthopaedics and Related Research,* No. 350, pp. 237–245, May 1998.

Clearfix Meniscal Screw instructional technique brochure, © 1998, Innovasive Devices, Inc.

*Primary Examiner*—Neill Wilson

*Attorney, Agent, or Firm*—Kolisch, Hartwell, Dickinson, McCormack & Heuser

[57] ABSTRACT

A screw having a root and threads formed on the root. The screw is configured to generate and/or maintain axial compression between threads formed in leading and trailing sections of the screw either by virtue of pitch differential in the threads or the way in which the screw is installed.

78 Claims, 5 Drawing Sheets

12 18 37 16 22 25 P 10 20 14 23 24 28 26

U.S. PATENT DOCUMENTS 3,664,540 5/1972 Witkin .
3,799,229 3/1974 Johnson .
3,915,162 10/1975 Miller .
4,058,856 11/1977 Doerre et al. .
4,059,102 11/1977 Devas .
4,069,980 1/1978 Yarem et al. .
4,175,555 11/1979 Herbert .
4,340,184 7/1982 Poss .
4,456,005 6/1984 Lichty .
4,463,753 8/1984 Gustilo .
4,468,200 8/1984 Munch .
4,537,185 8/1985 Stednitz .
4,640,271 2/1987 Lower .
4,723,541 2/1988 Reese .
4,842,464 6/1989 Green .
4,854,311 8/1989 Steffee .
4,863,383 9/1989 Grafelmann .
4,892,429 1/1990 Giannuzzi .
4,917,554 4/1990 Bronn .
4,940,467 7/1990 Tronzo .
4,950,270 8/1990 Bowman et al. .
4,959,064 9/1990 Engelhardt .
5,019,078 5/1991 Perren et al. .
5,019,079 5/1991 Ross .
5,042,982 8/1991 Harms et al. .
5,120,171 6/1992 Lasner .
5,147,363 9/1992 Harle .
5,180,382 1/1993 Frigg et al. .
5,252,016 10/1993 Schmid et al. .
5,259,398 11/1993 Vrespa .
5,300,076 4/1994 Leriche .
5,306,275 4/1994 Bryan .
5,403,136 4/1995 Mathys ................................ 411/263 X
5,443,509 8/1995 Boucher et al. .................... 411/412 X
5,456,685 10/1995 Huebner .............................. 411/395 X
5,470,334 11/1995 Ross et al. .
5,484,440 1/1996 Allard .
5,536,127 7/1996 Pennig .
5,562,672 10/1996 Huebner et al. .
5,569,252 10/1996 Justin et al. .
5,571,139 11/1996 Jenkins, Jr. .
5,601,553 2/1997 Trebing et al. ..................... 411/413 X
5,730,744 3/1998 Justin et al. .
5,735,653 4/1998 Schiefer et al. .
5,743,912 4/1998 Lahille et al. .
5,743,914 4/1998 Skiba .
5,746,039 5/1998 Nystrom .............................. 411/412 X
5,779,704 7/1998 Kim .
5,871,486 2/1999 Huebner et al. .

AXIAL TENSION SCREW

FIELD OF THE INVENTION

The present invention relates to fasteners and more particularly to a screw adapted to create axial tension along its length.

BACKGROUND OF THE INVENTION

Screws have long been used to secure objects to one another. Depending on the requirements of a particular application, the screw may take on many different shapes and sizes. Although screws have been produced in enormous variety, the vast majority create axial compression along the length of the screw by virtue of drawing the lower surface of a head down against the surface of one object using threads embedded in an adjacent object, as, for instance, occurs in a wood screw.

Although traditionally configured screws are suitable for most purposes, in some instances the presence of the head is unacceptable for functional, structural or cosmetic reasons. Various types of headless screws have been developed to address some of the applications where a traditional screw is less than optimal. One early example of such a screw is shown in U.S. Pat. No. 187,023 to Russell which employs a variable pitch thread to generate compression without relying on a head. Although the screw of Russell will generate some compression, its effectiveness is limited by the fact that the threads disposed toward the trailing end achieve little purchase because of the stripping that occurs due to the preceding threads of different pitch.

U.S. Pat. No. 4,175,555 to Herbert overcomes Russell's problem of reaming of female threads by subsequent threads on the screw. In particular, the Herbert screw has a region of large pitch and small diameter thread near the leading end and a region of smaller pitch and larger diameter thread near the trailing end, with the regions being separated by an unthreaded section. Unfortunately, the Herbert screw suffers from a number of other disadvantages. In the Herbert screw, the leading threads have a smaller diameter than the trailing threads. This is necessary to permit the leading threads to pass through the relatively large bore in the near bone fragment and engage the smaller bore in the remote bone fragment. The larger trailing threads then engage the larger bore in the near bone fragment As a result of this arrangement, any stripping of the threads cut into the bones during installation of the screw occurs in the remote bone. If the stripping occurred in the bore in the near bone fragment, a screw having a head thereon could still be used to compress the fracture even though the near bore was stripped; however, when stripping occurs in the bore in the remote bone, a standard screw with the head thereon cannot be used and another bore must be drilled.

Further, the Herbert screw must be correctly positioned, i.e., it is imperative that the fracture intersect the unthreaded central portion of the Herbert bone screw when the same is installed. Thus, the Herbert screw is not suitable for treating fractures that are very near the surface of the bone where the hole is to be drilled In addition, because the Herbert screw is not threaded entirely along the length thereof the purchase obtained by the screw in the bone is not as good as with a screw threaded along the entire length. Also, two bores of different sizes must be drilled to install the Herbert screw rather than a single bore.

Yet another problem with the Herbert screw is the stripping that can occur if additional tightening occurs after the screw has drawn the bone fragments together. While the bone fragments are being drawn together, trailing threads $K_6$ all follow a single path through the near fragment Similarly, leading threads $J_6$ all follow a single path through the remote fragment When, however, the bone fragments make contact, the two sets of threads can no longer move independently. Further rotation of the Herbert screw after contact between the fragments can cause the leading threads to strip out as they attempt to move forward through the distal bone fragment faster than the trailing threads will allow. See *The Herbert Bone Screw and Its Applications in Foot Surgery. The Journal of Foot and Ankle Surgery* No. 33, Vol. 4., 1994, pages 346–354, which reports on a study that found compression of 10 kg after only two complete turns of the trailing threads engaged in the near bone fragment Each subsequent revolution lead to a decrease in compressive force. Thus, care must be taken not to over-tighten the Herbert screw.

The various problems of the Herbert screw are addressed by the screw shown in U.S. Pat. No. 5,871,486, issued Feb. 16, 1999, to Huebner, which is herein incorporated by reference. The Huebner screw, sold under the trademark ACUTRAK, in most versions, is fully threaded and has a changing pitch over the entire length. The outside diameter of the thread tapers from front to rear so that as the trailing threads ream the tracks left by the leading threads due to the pitch change, the trailing threads are expanding outward into undisturbed material. The ACUTRAK screw can be driven in as far as desired without reduction in compression because of the expanding thread diameter along its length. In addition, the screw generates compression over the entire length, rather than only at the tip and tail as with Herbert. Thus, the ACUTRAK screw can be used to repair fractures anywhere along its length.

Although the ACUTRAK screw was a major improvement over the Herbert screw, installation of the ACUTRAK screw requires careful attention. In particular, the screw is typically installed in a tapered hole that has been pre-drilled. Drilling this tapered hole can be difficult because the tapered drill bit sometimes clogs with bone and tapered bits require more pressure to feed than a similar straight drill. Moreover, for best results, the depth of the hole should generally match the length of the screw, requiring the surgeon to drill the hole accurately. The other area of concern during installation is the torque needed to drive the screw. When the screw reaches the point where the root and hole taper match, the driving force increases substantially. Similarly, in dense bone, the driving force may make installation difficult.

DETAILED DESCRIPTION

Figure 1:
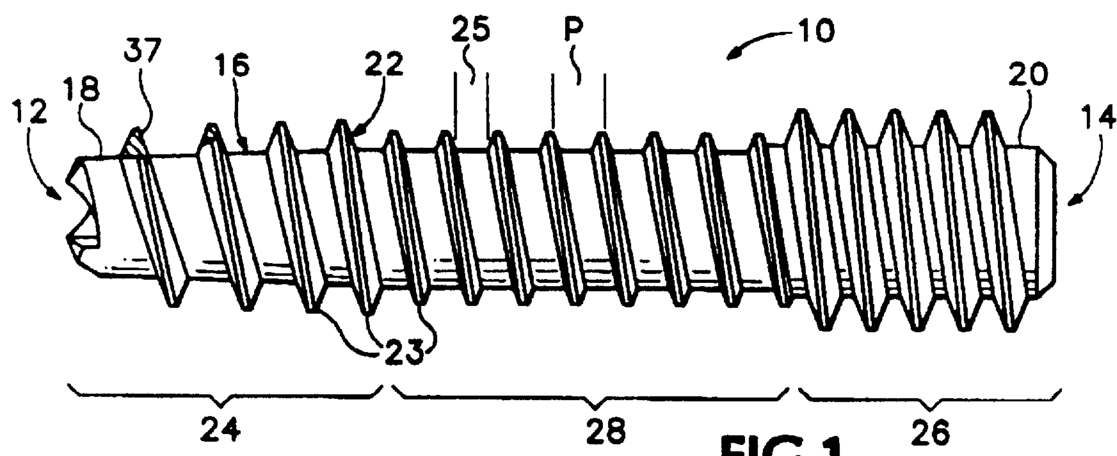
FIG. 1 is a side elevational view of a screw constructed according to the present invention.

A screw according to one embodiment of the present invention is shown at 10 in FIG. 1. Screw 10 extends between a front end 12 and a back end 14 and includes root portion 16. Root portion 16 has a leading end 18 and a tailing end 20, which, in the embodiment of FIG. 1, are coextensive with the leading and trailing ends of the screw. In other embodiments, the screw could extend beyond either end of the root portion.

A screw thread 22 is formed on root portion 16 and extends as a single continuous thread from the leading end to the trailing end. Screw thread 22 includes multiple thread revolutions 23, which are spaced apart on the root by an interthread spacing 25. It should be noted that the interthread spacing in combination with the thread depth establishes the pitch of the thread revolutions. In particular, increasing the interthread spacing or the thread depth (except in the case of perpendicular thread faces) increases the pitch. In screw 10, the interthread spacing is varied to avoid large pitch changes when reducing the outside diameter while at the same time maintaining a relatively constant root diameter. The reduced outside diameter and/or relatively constant root diameter helps to minimize the driving force required to advance the screw. It should also be noted that the thread land, the flat at the outside end of the thread, could also be varied to accommodate changing pitch.

One method of manufacturing screws according to the present invention is to use a computer-controlled screw machine or lathe. The threads are cut in repeated passes, typically with a single tool. The shape of the tool determines the thread face angle and the width at the tip of the tool determines the minimum interthread spacing. For larger interthread spacing, the position of the tool is shifted along the length of the screw on subsequent cutting passes to cut a wider interthread space. It should be noted that dimensions such as the interthread spacing and land are measured to a theorectical perfectly sharp comer even though, in practice, the corners may be rounded slightly or significantly.

The screw thread has a leading section 24 disposed toward the leading end, a trailing section 26 disposed toward the trailing end, and an intermediate, medial or waist section 28 disposed between the leading and tailing sections. The leading section has pitch which is larger at the leading end and decreases toward the trailing end. It should be noted that pitch, as used herein, is defined as the distance between corresponding points on consecutive threads as indicated at P in FIG. 1. With this pitch arrangement, the leading section generates axial compression between its ends as it is driven in. The outside diameter of the thread in the leading section tapers from a smaller diameter near the leading end to a larger diameter toward the trailing end at an angle of approximately 1.2 degrees relative to the elongate axis of the screw. The tapered outside diameter helps to prevent and/or mitigate the stripping of the leading threads in the object being secured that naturally occurs with threads of variable pitch or that may occur due to tension along the length of the screw. Typical taper angles or rates would generally be between 0.5 and 5 degrees.

Medial section 28 extends back from the end of leading section 24, but has an outside diameter that is reduced relative to the outside diameter of the thread at the trailing end of the leading section. The pitch of the medial section thread is less than the average pitch in the leading section and preferably, although not necessarily, approximately equal to the pitch at the back end of the leading section. This causes the medial section thread to maintain any compression or reduction generated by the leading section until the trailing section engages. The outside diameter of the thread can have a constant diameter, as illustrated, or may taper slightly outward toward the trailing end to accommodate any stripping that may occur because of the pitch difference between the leading section and the medial section. It should be noted that the medial section threads could be eliminated in favor of an unthreaded root, as described below.

The trailing section threads may be of constant diameter or may taper outwardly toward the trailing end. As with the leading section, the taper helps to reduce the effect of stripping because of changing pitch. The pitch of the threads in the trailing section is smaller than the pitch in the leading section so that as the screw moves forward, axial compression is generated along the length of the root. The pitch in the trailing section can be constant, as illustrated, or variable.

The root diameter tapers outwardly with the threads through the leading section and is constant in the medial and trailing sections, with the diameter through the trailing section being somewhat larger than the diameter through the medial section. Although the described root configuration is desirable to reduce the driving torque, the shape of the root can take many other forms essentially independent of the outside diameter of the threads.

Figure 2:
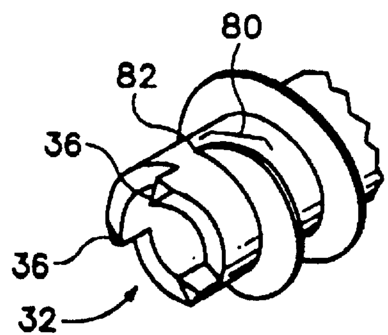
FIG. 2 is a perspective view of a self-cutting tip on the screw of FIG. 1.
Figure 3:
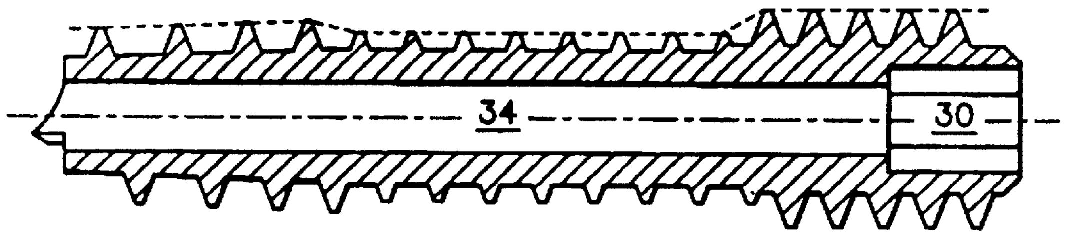
FIG. 3 is a cross-sectional view of the screw of FIG. 1.

Screw 10 includes a drive socket 30 at the trailing end and a self drilling tip 32 at the leading end. See FIGS. 2 and 3. A central bore 34 extends through the screw to facilitate installation of the screw over a guide wire. The self-drilling tip includes a plurality of teeth 36 disposed in a circular pattern around the periphery of the leading end, as shown in FIG. 2. Teeth 36 cut a path for the screw as it is advanced. A notch 37 in the threads at the front of the leading section may be provided to facilitate the thread on the screw tapping a female thread in the object to be fastened.

The leading section includes a termination zone 80 in which the thread diminishes rapidly to a starting point 82 on the root, as shown in FIG. 2. It should be noted that the root diameter is not diminishing commensurately with the thread diameter in the termination zone as occurs in a gimlet point screw. Although not essential to the present invention, the benefit of the depicted arrangement is that the thread diameter, and thus its holding power, is maintained to the end of the thread. This can be important where the joint to be secured falls near the front end of the screw. Both the self-cutting tip and termination zone could be used on any of the screws described herein. Alternatively, the tip of any of the screws could be pointed like more traditional screws to allow for self-starting with or without a pilot hole.

Screw 10, as shown, is particularly adapted for repair of bone fractures. In this application, screw 10 is formed of titanium, stainless steel, a resorbable substance, or some other biocompatible material. The screw may also incorporate an osteoductive substance to promote bone healing or growth. The osteoductive substance may be resorbable and form the structure of the screw or it may be a compound carried in the screw and delivered for instance through ports formed in the screw.

As depicted, screw 10 has a length of approximately 20 millimeters. Typical lengths in the range from a few millimeters to ten centimeters or more may be applicable to medical applications with the most common sizes ranging from about 10 to 40 millimeters. In non-medical uses, the length and size would be chosen to suit the particular application. The outside diameter of the leading section of screw 10 tapers from about 3.5 millimeters at the front to about 3.6 millimeters at the back, while the root tapers from about 2.4 to 2.5 millimeters over the same area. The root is cylindrical in the intermediate section with a diameter of 2.5 millimeters and cylindrical in the trailing section with a diameter of 2.8 millimeters. The outside diameter of the threads in intermediate and trailing sections is 3.2 and 4.1 millimeters, respectively.

In a typical screw, the pitch in the trailing section would be between 10 and 90 percent of the pitch in the leading section, with a pitch change around 50 percent, for example, being a typical value in orthopedic applications. It should be understood that greater or lesser pitch changes may be effective depending on the compression and reduction required for any particular application. In orthopedic applications, the pitch would typically fall in the range of between 10 and 100 thousandths of an inch.

Figure 4:
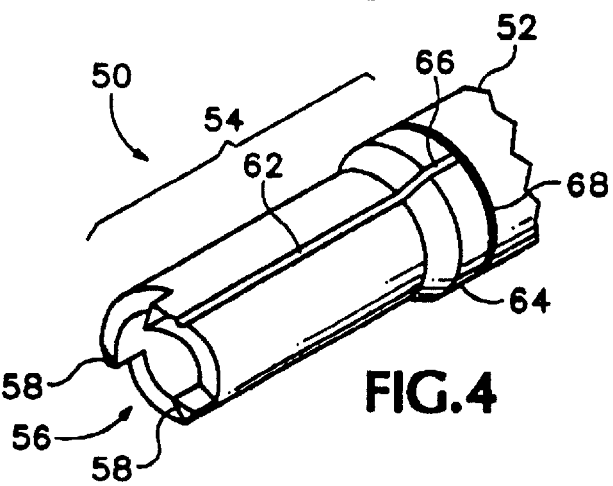
FIG. 4 is a perspective view of a drill for use with the screw of FIG. 1.

In the disclosed embodiment, a drill used to bore a hole to receive screw 10 is shown at 50 in FIG. 4. Drill 50 includes a cylindrical shank 52 to which a handle or motor, not shown, may be attached to allow manual or powered drilling. A cutting section 54 is formed on the leading end of the drill to create a hole of appropriate shape and size for the screw. The cutting section has a leading end 56 with cutting teeth 58, followed by a first cylindrical section 60, typically about 6–12 millimeters long, with a cutting flute 62. Adjacent the trailing end of the first cylindrical section, the cutting section tapers outward to a second cylindrical section 64 with a cutting flute 66. The diameter of the first cylindrical section is slightly, i.e., 0.005 inches, larger than the diameter of the root portion at the trailing end. The diameter of the second cylindrical section is approximately 0.020 inches larger than the diameter of the root section at the trailing end. The second section is larger because it is designed to form a slightly larger hole in the hard cortex shell of a bone so that passage of the trailing section of threads does not require excessive torque. A depth groove 68 is formed at the trailing end of the second cylindrical portion to be used as a gauge of proper hole depth during drilling. Drill 50 is cannulated so that it can be used over a guide wire.

Figure 5:
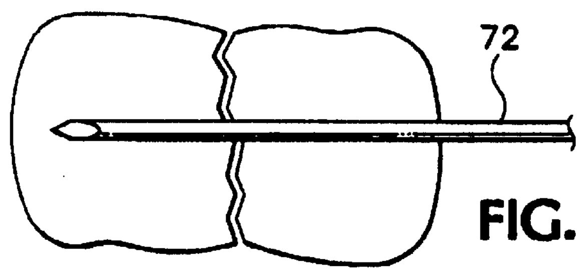
FIG. 5 shows the step of placing a guide wire into a bone in preparation for utilizing the screw of FIG. 1.
Figure 6:
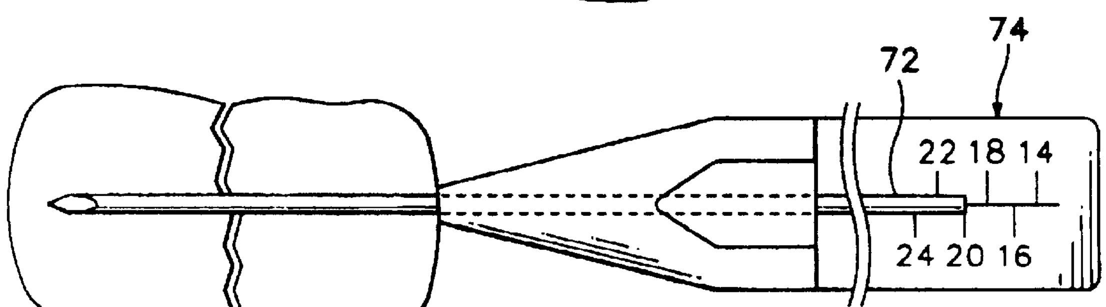
FIG. 6 shows use of a depth gauge to measure the length of screw required
Figure 7:
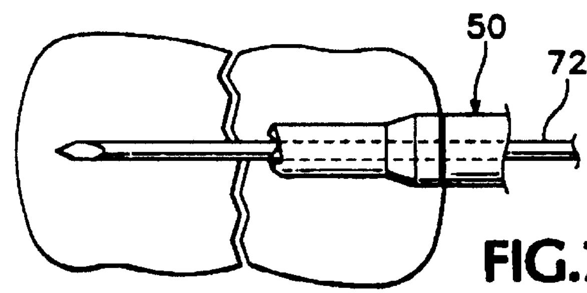
FIG. 7 shows use of the drill of FIG. 4.
Figure 8:
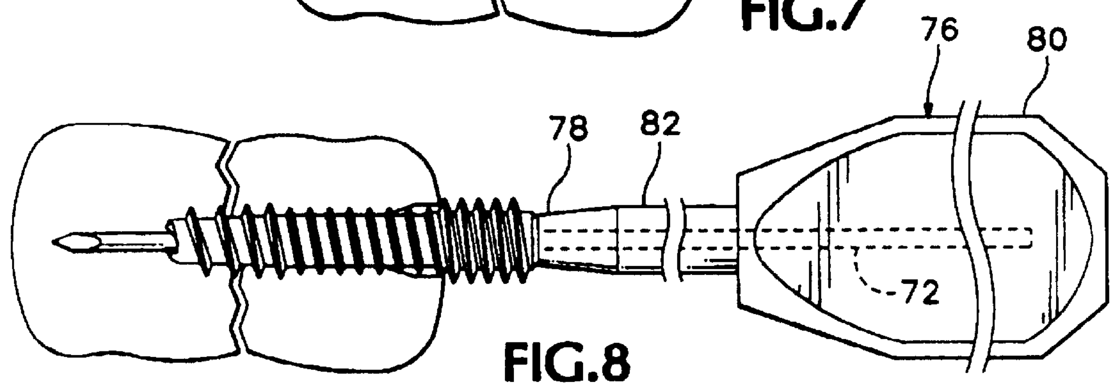
FIG. 8 shows the screw of FIG. 1 driven partially into the bone.
Figure 9:
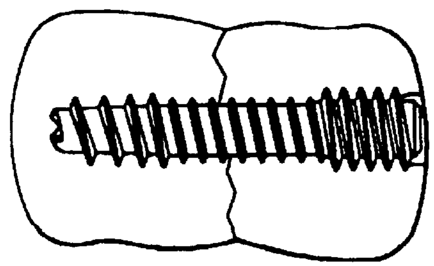
FIG. 9 shows the screw of FIG. 1 in its final placement.

To install screw 10 to repair a fractured bone, a surgeon will first place a guide wire 72, checking position and depth in the bone through x-ray as illustrated in FIG. 5. Next, the depth of the wire is measured using a template 74 which fits over the wire as shown in FIG. 6. Knowing the depth allows the surgeon to select a screw of the proper length. The drill is then installed over the guide wire and advanced until the depth groove reaches the surface of the bone. See FIG. 7. The screw is then slid over the wire, as shown in FIG. 8, and driven into the bone with the variable pitch generating axial compression along the length of the screw. The screw should be seated so that the trailing end is approximately 0.1 inches below the surface of the bone to avoid interference with surrounding tissues. See FIG. 9. The screw is driven in with a cannulated driver 76 having a driving tip 78, a handle 80 and a drive shank 82 extending between.

Figure 10:
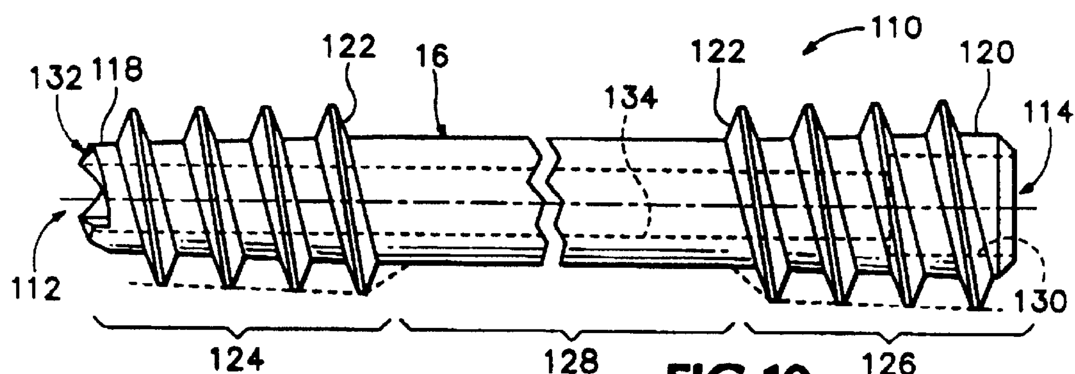
FIG. 10 shows another screw constructed according to the present invention.

FIG. 10 shows another screw according to the present invention. Screw 110 includes a front end 112, a back end 114 and a root portion 116. The root portion includes a leading end 118 and a trailing end 120. Screw 110 has a screw thread 122 formed thereon in a leading section 124 and a trailing section 126, with an unthreaded section 128 therebetween. The screw has a drive socket 130 and a drilling tip 132, similar to tip 32 on screw 10. As illustrated, the pitch of the screw thread in the leading and trailing sections is constant over each section, but the pitch could also vary over either or both sections depending on the type of compression sought. Screw 110 includes a central bore or cannulation 134.

Screw 110 is adapted for installation using a placement sleeve 140 as shown in FIGS. 11–14. Sleeve 140 includes a gripping structure 142 with a knurled perimeter 144 adapted to be gripped by an operator. Extending forward from the gripping structure is a shaft 146 leading to a contact tip 148. Contact tip 148 is preferably smooth and slightly rounded to allow it to rotate with minimal friction when pressed against an object. It is also possible, although not shown, that the tip could include some type of bearing connection to the shaft to eliminate the need for the tip to slide on the objection. The shaft includes an internal bore 150 which is threaded to match the threads in leading section 124 of screw 110. An elastomeric ring 152 is disposed inside bore 150 to frictionally connect the placement sleeve to the drive shank so that both turn as a unit unless the gripping structure is utilized to restrain the sleeve.

Figure 11:
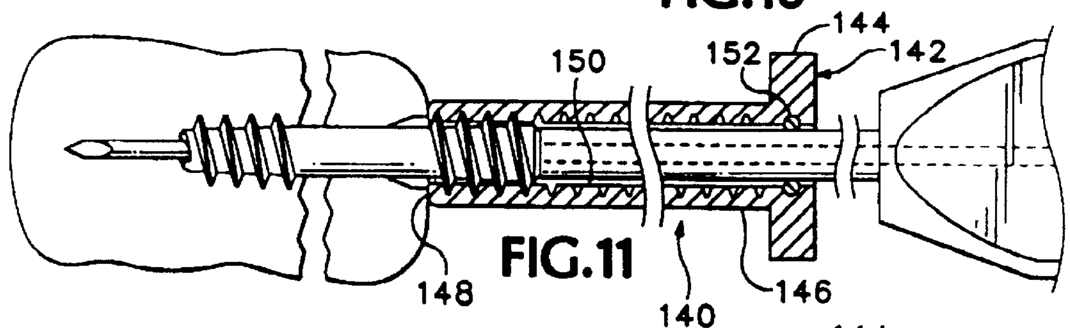
FIG. 11 shows the screw of FIG. 10 mounted to a sleeve and drive handle and partially installed in a fractured bone.
Figure 12:
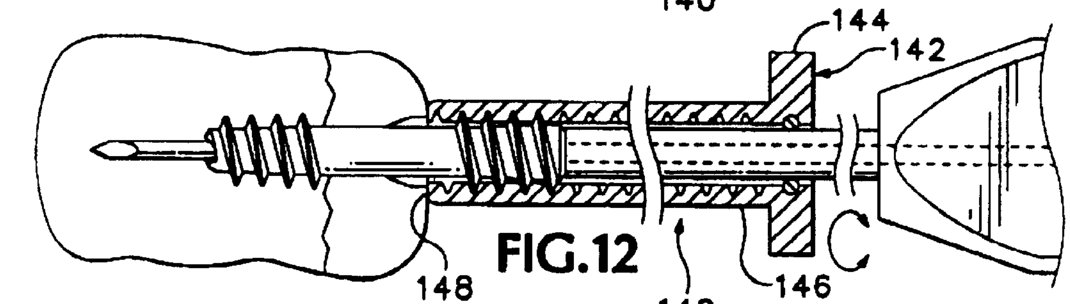
FIG. 12 shows the bone of FIG. 11 after reduction of the fracture by rotating the sleeve.
Figure 13:
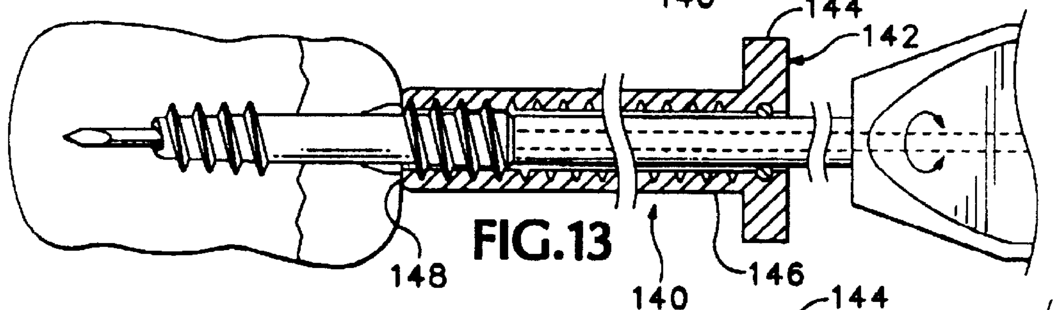
FIG. 13 shows the bone of FIG. 11 after reduction by rotating the sleeve and screw.
Figure 14:
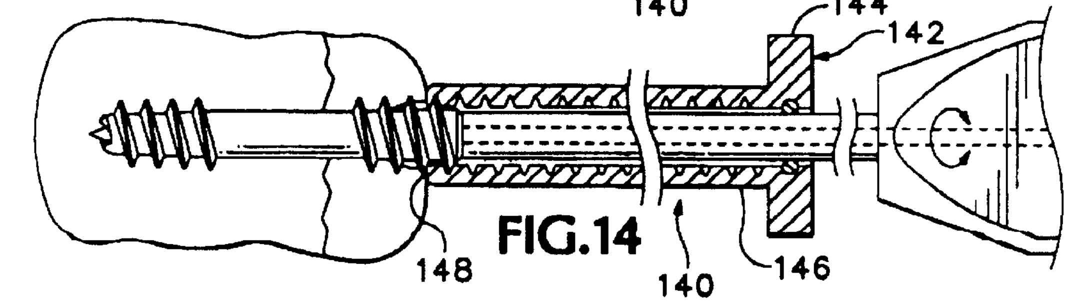
FIG. 14 shows the bone of FIG. 11 as the screw leaves the sleeve.

In use, the trailing end of screw 110 is screwed partially into bore 150, as shown in FIG. 11. The drive shank of the driver is then inserted into the bore from the opposite end. Mild pressure on the driver is sufficient to urge the shank through the elastomeric ring, although once the driver is slid into place, the ring prevents the sleeve from slipping off the driver. The screw, with the sleeve attached, is driven into the object to be secured until the leading section is buried and tip 148 contacts the surface of the object. Upon subsequent rotation of the driver and sleeve, tip 148 acts like the head of a standard screw and compression is generated along the axis of the screw, as shown by comparing FIGS. 11 and 13. This compression continues to build as long as the sleeve turns with the driver. To generate additional compression without driving the screw further into the object, the operator can rotate the sleeve using the gripping structure while holding the driver still, thus generating additional compression or reduction, as illustrated by the change between FIGS. 11 and 12. Once the desired compression/reduction is established, the operator holds the gripping structure while continuing to turn the driver, thus driving the trailing section threads out of the bore and into the member to be secured. See FIG. 14. The tension originally carried at the tip of the sleeve is thereby transferred to the trailing section threads.

It should be noted that the outside diameter of the threads in the leading and trailing sections of screw 110 is tapered. This taper, although not essential, is beneficial in that it makes the threads strip-tolerant. These sections of threads are strip-tolerant because the diameter of the threads expands toward the rear of the section. The expanding thread diameter brings all of the threads into contact with undisturbed material anytime the screw is moving forward in the object. Thus, even if the screw was momentarily stalled, stripping the female thread in the object, as soon as the screw starts to move forward, all of the threads find new purchase.

In a screw with a straight outside diameter, after any stripping occurs, only the threads at the leading end move into undisturbed material, leaving the remainder of the threads without purchase until they move forward far enough to pass the entire region where stripping occurred. Thus, a screw with a straight leading end is subject to abrupt and nearly complete loss of compression should any stripping occur. Moreover, the loss of compression is not recovered by simply driving the screw forward. This effect is manifest in the screw shown in Herbert, with which sudden loss of compression due to stripping of the leading threads is known to occur. In the case of Herbert, as with many of the screws disclosed herein, the stripping occurs due to the difference in pitch between threads in leading and trailing sections. In the case of screw 110 with the same pitch in both sections, stripping might occur as tension is created after the tip of the sleeve contacts the surface of the object.

Figure 15:
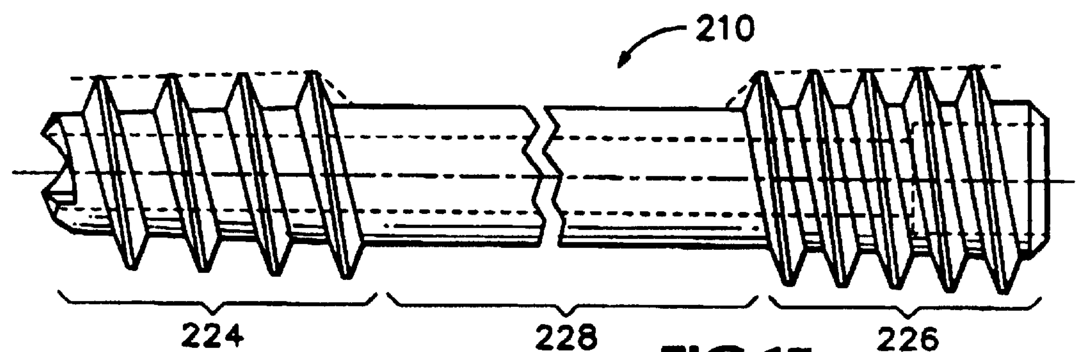
FIG. 15 shows a screw according to the present invention with an unthreaded intermediate section.

FIG. 15 shows a screw 210 similar to screw 110, but having a larger pitch in a leading section 224 and a smaller pitch in a trailing section 226 with an unthreaded medial section 228 in between. Although the pitch is different in each section, the pitch over each section is constant. Screw 210 can be used with sleeve 140 as described for screw 110, but can also generate compression without the sleeve because of the pitch differential. Although screw 210 is depicted with taper in the leading and trailing sections, taper could be used in only one of the sections depending upon the particular application. Moreover, the relative lengths of the two sections and the unthreaded section could be varied to suit the particular application.

Figure 16:
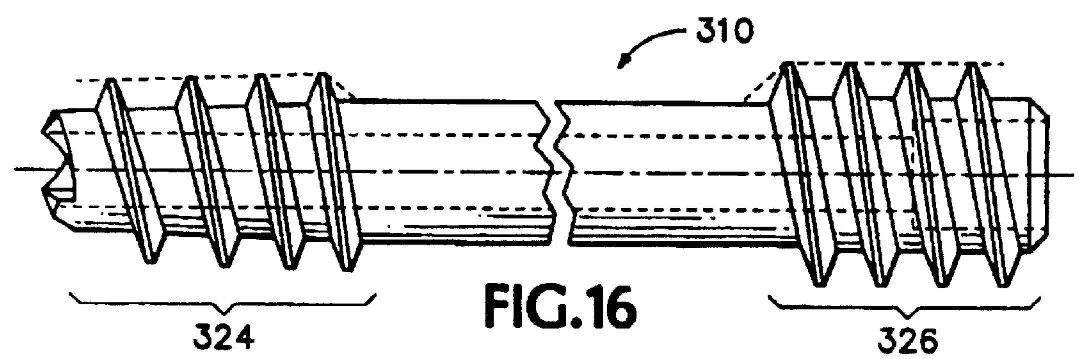
FIG. 16 shows a screw according to the present invention with an unthreaded intermediate section.

FIG. 16 shows a screw 310 similar to screw 110, but having a variable pitch in a leading section 324 and a constant pitch in a trailing section 326. As with screw 210, screw 310 can be used with or without the sleeve. The variable pitch threads in leading section 324 have a decreasing pitch moving toward the trailing end of the screw. Thus, the leading section threads develop some internal compression, in addition to the compression created between the leading and trailing sections, which may be beneficial where additional compression or reduction is desired near the leading end.

It should be understood that the screws of the various embodiments shown herein could also have a variable pitch in the trailing section to create additional compression. As long as the pitch change was not too large, such screws could still be used with the sleeve by providing a slightly looser fit to the threads in the sleeve or a sleeve with an interior surface which is soft enough to be deformed by the threads on the screw.

Figure 17:
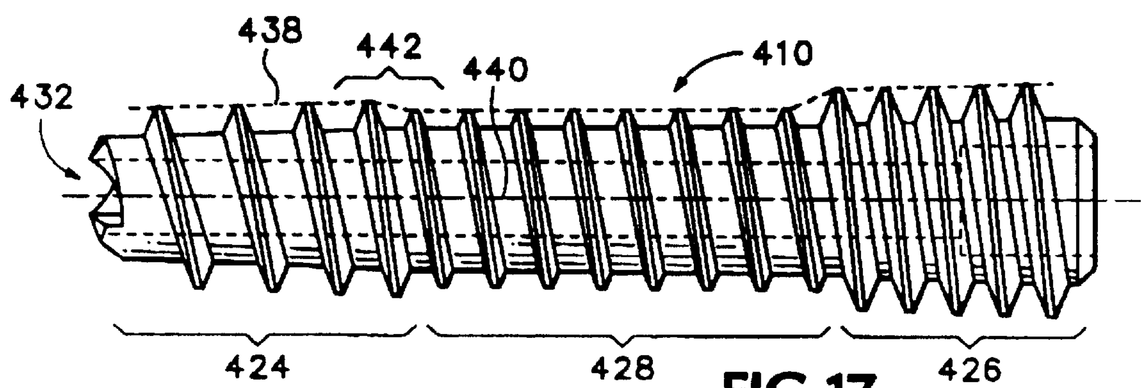
FIG. 17 shows another screw according to the present invention.

FIG. 17 shows a screw 410 having a leading section 424, a trailing section 426 and an intermediate section 428. Each section is threaded and has the same pitch pattern as shown in screw 10. Also like screw 10, screw 410 includes a self-drilling tip 432 and a central bore 434. Screw 410 differs from screw 10 in that the outside diameter of the screw tapers outward even in the intermediate section. In particular, as shown, screw 410 tapers at around 2 degrees over the leading and trailing sections and about ½ degree over the intermediate section. The reduction in taper angle over the intermediate section reduces the driving force required to install the screw while providing some additional grip in the intermediate section relative to screw 10. It should be noted that the intermediate section could also have no taper or taper in toward the trailing end.

Dashed line 438 indicates the shape of a surface of revolution of the threads about an elongate axis 440 of the screw, as similarly illustrated on other embodiments. It can be seen that the surface of revolution has a constriction or steps in slightly in the area 442 of the transition between the leading section and the intermediate section. The surface is then steps out in the area of the transition between the intermediate section and the trailing section.

Figure 18:
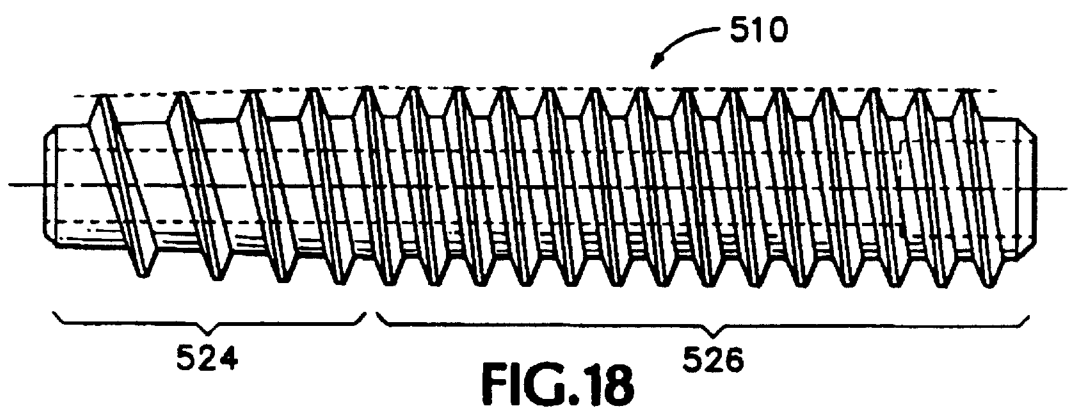
FIG. 18 shows a screw according to the present invention with a cylindrical trailing section.

FIG. 18 shows a screw 510 having a leading section 524 and a trailing section 526. The leading section has variable pitch which is larger near the front end of the screw and decreases back toward the trailing section. The threads in the trailing section are constant pitch and start at the same pitch as at the trailing end of the leading section. The leading section is shorter than the trailing section and constitutes approximately ⅓ of the length of the threaded sections. The outside diameter or surface of revolution of the threads at transition between the leading section and trailing section makes a convex transition. The trailing section is depicted with constant outside diameter, but could alternatively have a taper. Similarly, while the pitch is depicted as constant, variable pitch could be used, depending on the compression desired.

Figure 19:
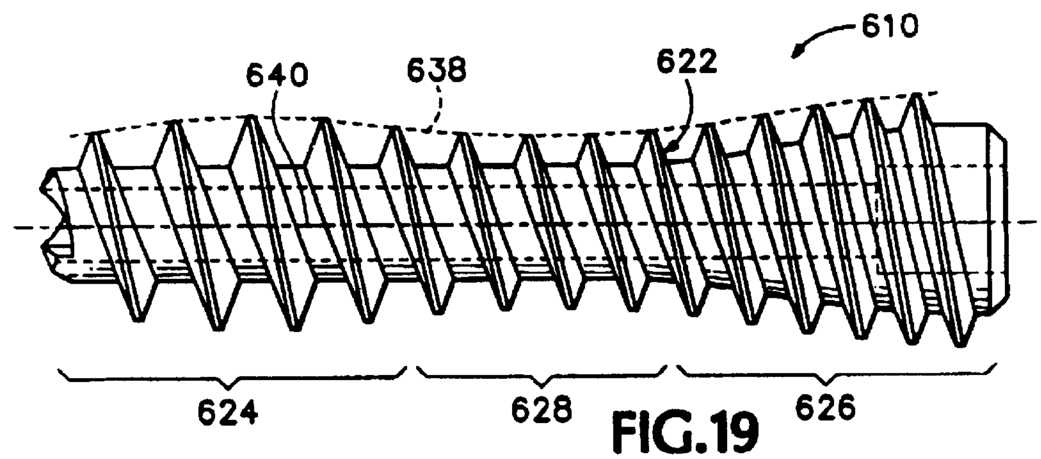
FIG. 19 shows a screw according to the present invention with a smoothly changing outside diameter.

FIG. 19 shows a screw 610 having a leading section 624, a trailing section 626 and an intermediate or waist portion 628. A single continuous screw thread 622 extends over all three sections and has a pitch which changes relatively constantly over the entire length. As before, other pitch patterns could be used, such as constant pitch in the leading and trailing sections and variable pitch in the intermediate section. The thread revolutions on screw 610, as with the other screws disclosed herein, can be considered to form a surface of revolution about an elongate axis 640 of the screw, the surface being indicated by dashed line 638. The surface of revolution of screw 610 smoothly changes with no abrupt discontinuities in slope or diameter. The surface of revolution is convex in the area of the transition between the leading and intermediate sections and is concave in the area of the transition to the trailing section. Screw 610 includes a central bore 634 and a self-drilling tip 632.

Figure 20:
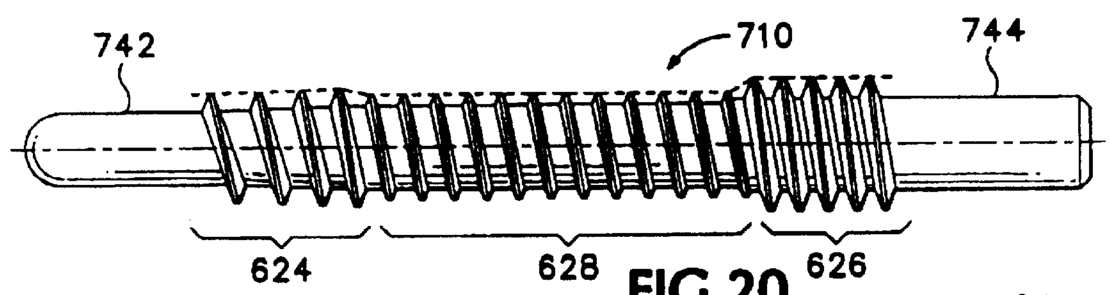
FIG. 20 shows a screw according to the present invention with unthreaded leading and trailing extensions.

FIG. 20 shows a screw 710 similar to screw 10, but having an unthreaded leading extension 742 and an unthreaded trailing extension 744. The unthreaded extensions are useful to resist bending loads along the axis of the screw, such as where two elongate members are secured together. Screw 710 is thus useful in, for instance, interphalangeal fusion procedures. Although the extensions are illustrated on a screw such as screw 10, it should be understood that they could be applied to any of the other screws depicted herein.

Figure 21:
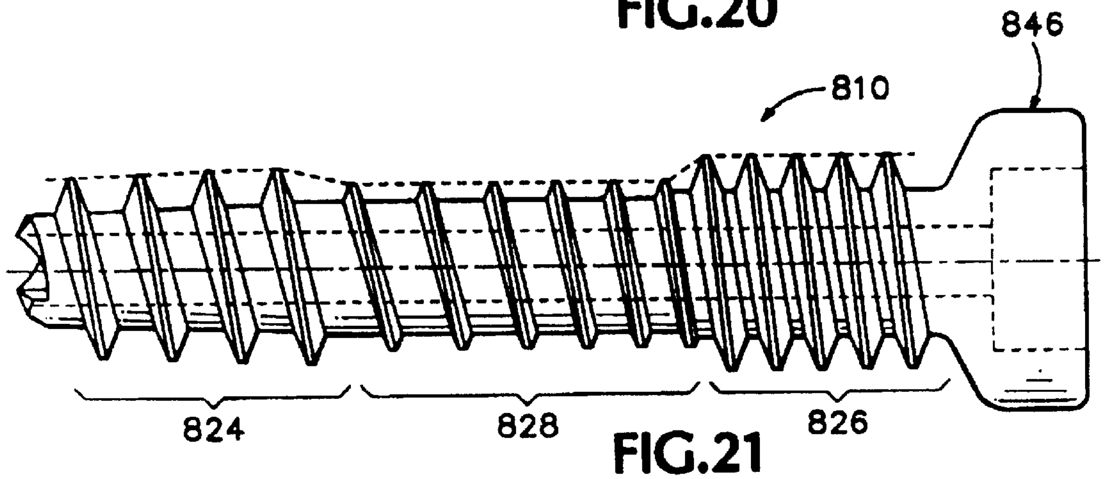
FIG. 21 shows a headed screw according to the present invention.

FIG. 21 illustrates a screw 810 similar in profile to screw 10, but further including a head 846. Screw 810 includes a leading section 824 of constant pitch, a trailing section 826 of constant but smaller pitch and an intermediate section 828 of variable pitch connecting the leading and trailing sections. It should be understood that this pitch pattern and outside diameter profile is not specific to or required by a headed screw according to the present invention and other embodiments shown herein could be equipped with a head. Although the head creates the disadvantage that the screw cannot be driven in below the surface of the objects to be fastened, it may be useful under some circumstances, such as where the screw may serve as an anchor or hold down a plate.

Figure 22:
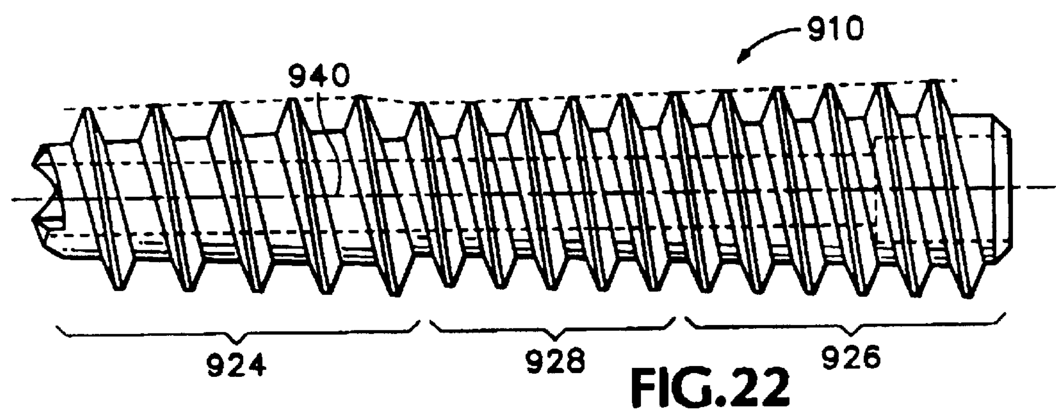
FIG. 22 shows a screw according to the present invention with a stepped, tapered outside diameter.

FIG. 22 depicts a screw 910 having a leading section 924, a trailing section 926 and an intermediate or waist section 928. The leading section is frustro-conical in shape and tapers at an angle of approximately 2 degrees relative to an elongate axis 940 of the screw. The thread revolutions in the intermediate section have an outside diameter which is stepped down from the trailing end of the leading section to approximately the starting diameter of the leading section. The outside diameter of the thread revolutions in the intermediate section then tapers outward smoothly into the trailing section. The intermediate and trailing sections thus have a frustro-conical profile, again at an angle of approximately 2 degrees. The leading section represents about ⅓ of the length of the screw, although other ratios could of course be used. As depicted, the pitch of the threads in the leading section is constant. The pitch of the threads in the intermediate and trailing section is also constant, but smaller than the pitch in the leading section. The pitch of the threads in any or all of the leading, intermediate and trailing sections could also be variable.

Although the various screws according to the present invention disclosed herein are described with particular reference to orthopedic applications, it should be understood that screw designs according to the present invention could be used for other fastening purposes as well. For instance, screws according to the present invention could be used to fasten wood flooring to subfloors, sheathing or gypsum board to studs and many other non-medical uses. Generally, screws according to the present invention are particularly useful where compression is needed or two objects must be secured together, but where the head of a standard screw or nail would be undesirable for functional or cosmetic reasons.

While the invention has been disclosed in its preferred form, the specific embodiments thereof as disclosed and illustrated herein are not to be considered in a limiting sense as numerous variations are possible. Applicant regards the subject matter of his invention to include all novel and non-obvious combinations and subcombinations of the various elements, features, functions and/or properties disclosed herein. No single feature, function, element or property of the disclosed embodiments is essential. The following claims define certain combinations and subcombinations which are regarded as novel and non-obvious. Other combinations and subcombinations of features, functions, elements and/or properties may be claimed through amendment of the present claims or presentation of new claims in this or a related application. Such claims, whether they are broader, narrower or equal in scope to the original claims, are also regarded as included within the subject matter of applicant's invention.

I claim:

1. A fastener comprising:

a root portion, the root portion having a leading end, a trailing end and an elongate axis extending therebetween; and a single continuous thread formed on the root portion and extending between the leading end and the trailing end of the root portion, the thread having an outside diameter which, moving from the leading end toward the trailing end, increases over several revolutions, then decreases, then increases again, wherein the pitch of the thread measured between corresponding points on consecutive threads near the leading end is larger than the pitch of the threads near the trailing end.

2. The fastener of claim 1, wherein the root portion includes a bore extending along the elongate axis from the leading end to the trailing end.

3. The fastener of claim 1, wherein the thread includes an interthread spacing between revolutions of the thread on the root portion and further wherein the interthread spacing varies along the root portion.

4. The fastener of claim 3, wherein the thread includes an intermediate region disposed generally between the leading end and the trailing end, and further wherein the interthread spacing is larger in the intermediate region than near the trailing end.

5. The fastener of claim I further including a self-drilling tip disposed at the leading end of the root portion.

6. The fastener of claim 1, wherein the thread includes an intermediate portion where the outside diameter is decreased and over which the outside diameter of the threads is substantially constant.

7. A screw comprising a leading section having a plurality of thread revolutions, a trailing section having a plurality of thread revolutions and an unthreaded intermediate section between the leading and trailing sections, the thread revolutions in the leading section having a greater average pitch and smaller average outside diameter than the thread revolutions in the trailing section, and where the outside diameter of the thread revolutions in the leading section generally increases toward the trailing section.

8. The screw of claim 7, wherein the outside diameter of the thread revolutions in the leading section tapers outward toward the trailing section at an angle of 0.5 to 2.5 degrees relative to an elongate axis of the screw.

9. The screw of claim 7, wherein the leading section includes at least three thread revolutions.

10. The screw of claim 7, wherein the pitch of the thread revolutions in the leading section decreases toward the trailing section.

11. The screw of claim 7, wherein the outside diameter of the thread revolutions in the trailing section generally increases away from the leading section.

12. The screw of claim 7, wherein the intermediate section has a smaller average diameter than the leading section.

13. The screw of claim 7, wherein the pitch of the thread revolutions in the trailing section is constant.

14. The screw of claim 7, wherein the screw includes a central bore extending through the screw along an elongate axis.

15. The screw of claim 7, wherein the screw is headless.

16. A screw comprising a leading end, a leading section proximal to the leading end and having a plurality of thread revolutions, a trailing end, a trailing section proximal the trailing end and having a plurality of thread revolutions, and a waist section having at least one thread revolution disposed between the leading and trailing sections, the thread revolutions in the leading section having a greater average pitch and smaller maximum outside diameter than the thread revolutions in the trailing section, and wherein the minimum outside diameter of the at least one thread revolution in the waist section is less than the maximum outside diameter of the thread revolutions in the leading section.

17. The screw of claim 16, wherein the outside diameter of the thread revolutions in the leading section is smaller toward the leading end and larger toward the trailing end.

18. The screw of claim 16, wherein the pitch of the threads in the leading section is larger toward the leading end and smaller toward the trailing end.

19. The screw of claim 16, wherein the minimum outside diameter in the waist region is at least five percent smaller than the maximum outside diameter in the leading section.

20. The screw of claim 16 further including a root portion on which the thread revolutions are formed and where the thread revolutions are the only part of the screw with a larger diameter than the root portion.

21. The screw of claim 20, wherein the thread depth measured between the root portion and the outside diameter of the thread revolutions is at least as large near the leading end as the change in outside diameter of the thread revolutions between the leading and trailing sections.

22. The screw of claim 20, wherein the thread depth in the leading section is at least substantially as large as the radius of the root portion in the leading section.

23. The screw of claim 20, wherein the root portion is substantially cylindrical over at least one of the sections.

24. The screw of claim 16, wherein the maximum diameter of the thread revolutions is at least equal to the largest diameter of any part of the screw.

25. The screw of claim 16, wherein, at least along part of the screw, the pitch gradually decreases as the outside diameter gradually increases.

26. The screw of claim 16, wherein the pitch changes substantially continuously over the majority of the threaded sections.

27. A screw comprising a leading section having a plurality of thread revolutions, a trailing section having a plurality of thread revolutions and an intermediate section between the leading section and the trailing section, the thread revolutions in the leading section having a greater average pitch and smaller maximum outside diameter than the thread revolutions in the trailing section, the intermediate section having a smaller average outside diameter than the leading or trailing sections and where the outside diameter of the thread revolutions in the leading section generally increases from revolution to revolution toward the trailing section.

28. The screw of claim 27, wherein the intermediate section includes a plurality of thread revolutions.

29. The screw of claim 28, wherein the thread revolutions in the leading, intermediate and trailing sections form a single continuous thread.

30. The screw of claim 28, wherein the outside diameter of the thread revolutions in the intermediate section is substantially constant.

31. The screw of claim 28, wherein the outside diameter of the thread revolutions in the leading section tapers outward toward the trailing section at an average angle of approximately 0.8 to 3 degrees.

32. The screw of claim 27, wherein the average pitch of the thread revolutions in the trailing section is less than about 90 percent of the average pitch of the thread revolutions in the leading section.

33. The screw of claim 27, wherein each section covers at least 10 percent of the length of the screw.

34. The screw of claim 27, wherein the screw has an elongate axis and includes a bore extending through the screw along the elongate axis.

35. The screw of claim 27, wherein the outside diameter of the thread revolutions in the leading section tapers at an angle of between 0.5 and 5 degrees relative to an elongate axis of the screw.

36. The screw of claim 27, wherein the pitch of the thread revolutions in the leading section is substantially constant.

37. The screw of claim 27, wherein the pitch of the thread revolutions in the trailing section is substantially constant.

38. The screw of claim 27, wherein the average pitch of the thread revolutions in the trailing section is at least substantially half of the average pitch of the thread revolutions in the leading section.

39. The screw of claim 27, wherein the intermediate section is unthreaded.

40. The screw of claim 39, wherein the intermediate section covers at least 20 percent of the length of the screw.

41. The screw of claim 27, wherein the pitch of the thread revolutions in the leading section decreases toward the trailing section.

42. The screw of claim 27, wherein the pitch of the thread revolutions in the trailing section increases toward the leading section.

43. The screw of claim 27, wherein the outside diameter of the thread revolutions in the trailing section decreases toward the leading section.

44. The screw of claim 27 further comprising an unthreaded extension projecting from an end of the leading section opposite the trailing section.

45. The screw of claim 27 further comprising an unthreaded extension projecting back from an end of the trailing section opposite the leading section.

46. A screw comprising a leading section having a plurality of thread revolutions, a trailing section having a plurality of thread revolutions and an intermediate section disposed between the leading section and the trailing section and having a plurality of thread revolutions, the outside diameter of the thread revolutions forming a surface of revolution about an elongate axis of the screw, the surface of revolution being convex in the transition from the leading section to the intermediate section and concave in the transition from the intermediate section to the trailing section, and wherein the thread revolutions in the leading section have a greater average pitch and smaller maximum outside diameter than the thread revolutions in the trailing section.

47. The screw of claim 46, wherein the surface of revolution is generally conical in the leading section.

48. The screw of claim 46, wherein the surface of revolution is generally cylindrical in the trailing section.

49. The screw of claim 46 further including a root portion extending through the leading, intermediate and trailing sections, wherein the diameter of the root portion is substantially constant through the leading section and the intermediate section.

50. The screw of claim 49, wherein the root portion has a leading end and a trailing end and a central bore extending therebetween.

51. The screw of claim 48, wherein the surface of revolution tapers generally outward at an average angle of between 0.5 and 5 degrees relative to the elongate axis over the leading section.

52. The screw of claim 46 further including a root portion, and further wherein there is a termination zone in the thread revolutions in the leading section in which the thread revolutions diminishes from approximately the average outside diameter of the thread revolutions in the leading section down to a starting point on the root portion, and wherein the diameter of the root portion does not diminish substantially in the termination zone and the outside diameter of the thread revolutions in the leading section generally increases from revolution to revolution outside the termination zone.

53. The screw of claim 52, wherein the termination zone includes less than one thread revolution.

54. The screw of claim 46, wherein the surface of revolution is generally conical in the trailing section.

55. The screw of claim 46, wherein no part of the screw has a larger diameter than maximum diameter of the thread revolutions.

56. The screw of claim 46, wherein the thread revolutions in the three sections form a single, substantially continuous thread.

57. The screw of claim 46, wherein the surface of revolution tapers outward at an angle of approximately 0.5 to 5 degrees in the leading section.

58. The screw of claim 46, wherein the average pitch in the leading section is at least 10% larger than the average pitch in the trailing section.

59. The screw of claim 46, wherein each section extends for at least 15% of the total length of the three sections along the elongate axis.

60. The screw of claim 46, wherein the pitch of the thread revolutions in the leading section is substantially constant.

61. The screw of claim 46, wherein the pitch of the thread revolutions in the trailing section is substantially constant.

62. The screw of claim 46, wherein the pitch of the thread revolutions in at least one of the sections is variable.

63. The screw of claim 62, wherein the pitch is variable in the intermediate section.

64. The screw of claim 62, wherein the pitch is variable in all three sections.

65. The screw of claim 46 further comprising an unthreaded leading extension disposed at an end of the leading section opposite the trailing section.

66. The screw of claim 46 further comprising an unthreaded trailing extension disposed at the end of the trailing section opposite the leading section.

67. The screw of claim 46, wherein the screw is formed of a biocompatible material.

68. The screw of claim 67, wherein the screw is formed of a resorbable material.

69. The screw of claim 68, wherein the resorbable material is osteoductive.

70. The screw of claim 46, wherein the combined length of the three sections is between 0.5 inches and 4 inches.

71. The screw of claim 46 further comprising a root portion on which the thread revolutions are formed, and wherein the thread revolutions have an interthread spacing on the root portion, and further wherein the interthread spacing on the root is not constant over the three sections.

72. The screw of claim 46 further comprising a self-cutting tip disposed at the end of the leading section opposite the trailing section.

73. The screw of claim 46 further comprising a head.

74. A screw comprising a leading section having a plurality of thread revolutions and a trailing section having a plurality of thread revolutions and forming a continuous extension of the thread revolutions of the leading section, the outside diameter of the thread revolutions forming a surface of revolution about an elongate axis of the screw, the surface of revolution being convex in the transition from the leading section to the trailing section, and wherein the thread revolutions in the leading section have a greater average pitch and smaller average outside diameter than the thread revolutions in the trailing section and the length of the leading section is less than the length of the trailing section, the screw further including a root portion and wherein there is a termination zone in the thread revolutions in the leading section in which the thread revolutions diminish from approximately the average outside diameter of the thread revolutions in the leading section down to a starting point on the root portion, and wherein the diameter of the root portion does not diminish substantially in the termination zone whereby the screw has a relatively blunt leading end.

75. The screw of claim 74, wherein the outside diameter of the thread revolutions in the leading section generally increases from revolution to revolution outside the termination zone.

76. The screw of claim 75, wherein the surface of revolution in the leading section tapers at an angle of between 0.5 and 5 degrees relative to the elongate axis of the screw outside the termination zone.

77. The screw of claim 74, wherein the pitch of the thread revolutions gradually decreases in the leading section toward the trailing section.

78. The screw of claim 74, wherein the screw is headless.

* * * * *